US009675960B2

(12) United States Patent
Goerlich et al.

(10) Patent No.: US 9,675,960 B2
(45) Date of Patent: Jun. 13, 2017

(54) IMMOBILIZATION OF CHELATING GROUPS FOR IMMOBILIZED METAL ION CHROMATOGRAPHY (IMAC)

(71) Applicant: Max-Planck-Gesellschaft zur Foerderung Der Wissenschaften e.V., Munich (DE)

(72) Inventors: Dirk Goerlich, Goettingen (DE); Steffen Frey, Goettingen-Herberhausen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/723,770

(22) Filed: May 28, 2015

(65) Prior Publication Data
US 2015/0283536 A1 Oct. 8, 2015

Related U.S. Application Data

(62) Division of application No. 12/672,345, filed as application No. PCT/EP2008/006485 on Aug. 6, 2008, now Pat. No. 9,073,971.

(60) Provisional application No. 60/954,144, filed on Aug. 6, 2007.

(30) Foreign Application Priority Data

Aug. 6, 2007 (EP) .................... 07015389
Jul. 14, 2008 (EP) .................... 08012686

(51) Int. Cl.
*C07K 1/22* (2006.01)
*B01J 20/32* (2006.01)
*B01D 15/38* (2006.01)
*B01J 45/00* (2006.01)
*C07K 1/13* (2006.01)
*B01J 20/286* (2006.01)

(52) U.S. Cl.
CPC ...... *B01J 20/3219* (2013.01); *B01D 15/3828* (2013.01); *B01J 20/286* (2013.01); *B01J 20/3251* (2013.01); *B01J 20/3265* (2013.01); *B01J 45/00* (2013.01); *C07K 1/13* (2013.01); *C07K 1/22* (2013.01)

(58) Field of Classification Search
None
See application file for complete search history.

(56) References Cited

U.S. PATENT DOCUMENTS

| 4,407,978 A | 10/1983 | Kahovec et al. |
| 4,423,158 A | 12/1983 | Porath |
| 4,965,211 A | 10/1990 | Wieder et al. |
| 5,594,115 A | 1/1997 | Sharma |
| 5,962,641 A | 10/1999 | Nelson et al. |
| 6,399,750 B1 | 6/2002 | Johansson |
| 6,441,146 B1 | 8/2002 | Minh |
| 6,551,515 B1 * | 4/2003 | Bruening ................. B01J 20/32 210/670 |
| 6,593,120 B1 | 7/2003 | Riggs et al. |
| 6,670,159 B1 | 12/2003 | Savage et al. |
| 6,872,317 B1 | 3/2005 | Nambu et al. |
| 7,112,552 B2 | 9/2006 | Simpson et al. |
| 2002/0094566 A1 | 7/2002 | Tubbs et al. |
| 2002/0143158 A1 | 10/2002 | Perry et al. |
| 2002/0164718 A1 | 11/2002 | Tchaga et al. |
| 2004/0185545 A1 | 9/2004 | Simpson et al. |
| 2004/0204569 A1 | 10/2004 | Radmacher et al. |
| 2005/0272116 A1 | 12/2005 | Ellison et al. |
| 2010/0016564 A1 | 1/2010 | Andersson et al. |

FOREIGN PATENT DOCUMENTS

| AE | 1767631 A | 3/2007 |
| CN | 1580252 A | 2/2005 |
| CN | 1922310 A | 2/2007 |
| CN | 1997671 A | 7/2007 |
| EP | 0 635 733 A1 | 1/1995 |
| EP | 07 015 389.5 | 8/2007 |
| EP | 08 012 686.5 | 7/2008 |
| GB | 2067203 A1 | 7/1981 |
| GB | 2183238 A | 6/1987 |
| SE | 0701682-7 | 7/2007 |
| WO | 91/15504 A1 | 10/1991 |
| WO | 92/17403 A | 10/1992 |
| WO | 0181365 A | 11/2001 |
| WO | 2004036189 A | 4/2004 |
| WO | 2004/104023 A2 | 12/2004 |
| WO | 2005089933 A | 9/2005 |
| WO | 2005/120700 A | 12/2005 |

(Continued)

OTHER PUBLICATIONS

Ethylene glycolbis(2aminoethylether)N,N,N',N'tetraaceticacid; Sigma-Aldrich, obtained Jul. 25, 2016; p. 1;www.sigmaaldrich.com/catalog/search?term=EGTA&interface=All&N=0+&mode=partialmax&lang=en&region=US&focus=product#.*
N-(3-Dimethylaminopropyl)-N'-ethylcarbodiimide hydrochloride; Sigma-Aldrich; obtained Jul. 25, 2016; p. 1;www.sigmaaldrich.com/catalog/search?term=EDC&interface=All&N=0&mode=match%20partialmax&lang=en&region=US&focus=product#.*
Extended European Search Report issued in European Divisional Application 14173856.7 dated Jan. 7, 2016, 24 pages.
Kahovec et al., "EDTA Ester of Bead Cellulose a Fast-Kinetics Chelating Sorbent", Polymer Bulletin, 3, 13-17, (1980).
S. Govender: "A Pluronic-Coupled Metal-Chelating Ligand for Membrane Affinity Chromatography", Journal of Membrane Science, vol. 279, 2006,pp. 120-128.
Haner et al., "Synthesis of a New Chelating Gel: Removal of Ca2+ Ions from Parvalbumin", Analytical Biochemistry, 1984, pp. 229-234.

(Continued)

Primary Examiner — Lianko Garyu
(74) Attorney, Agent, or Firm — Rothwell, Figg, Ernst & Manbeck, P.C.

(57) ABSTRACT

The present invention refers to a method for binding a polycarboxylic acid to a solid phase. Further, the invention refers to a solid phase having a polycarboxylic acid immobilized thereto and methods of using the solid phase, e.g. for purifying His-tagged recombinant polypeptides.

10 Claims, 8 Drawing Sheets

(56) References Cited

FOREIGN PATENT DOCUMENTS

Figure 1:
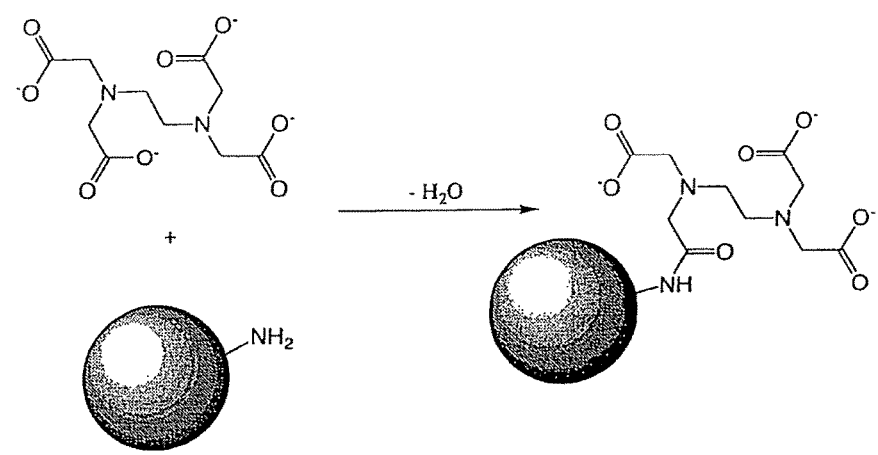

WO    2007139470 A1    12/2007
WO    2009/008802 A1    1/2009

OTHER PUBLICATIONS

Waugh, "Making the most of affinity tags", TRENDS in Biotechnology, 2005, pp. 316-320.
Amersham Biosciences, The Recombinant Protein Handbook. Protein Amplification and Simple Purification, Edition AB, Chapter 4 "(His)6 Fusion Proteins", 2001, 112 pages.
Amersham Biosciences: "Purification of (His)6-tagged proteins using HiTrap Chelating HP columns charged with different metal ions", application note, Affinity chromatography, 2002.
Bornhorst et al.: "Purification of Proteins Using Polyhistidine Affinity Tags", Methods Enzymol., vol. 326, 2000, pp. 245-254.
Heijbel: "Purification of a protein tagged with (His)6 at its N-terminus, C-terminus, and both N- and C-termini using different metal ions", Life Science News, vol. 15, 2003, pp. 22-24.
Porath et al.: "Immobilized Metal Ion Affinity Adsorption and Immobilized Metal Ion Affinity Chromatography of Biomaterials. Serum Protein Affinities for Gel-Immobilized Iron and Nickel Ions", Biochemistry, vol. 22, 1983, pp. 1621-1630.
Protein Purification: Principles, High-Resolution Methods, and Applications, editors Janson & Ryden, 1998, 4 pages.
Rahman et al.: "Characterization of an EDTA Bonded Conducting Polymer Modified Electrode: Its Application for the Simultaneous Determination of Heavy Metal Ions", Anal. Chem., vol. 75, 2003, pp. 1123-1129.
Declaration by Professor Dirk Goerlich, dated Jan. 24, 2017, 20 pages.
Purification of Polyhistidine—Tagged Proteins, Machery-Nagel, Rev. 03, published Apr. 2006, 44 pages.
Purification of Polyhistidine—tagged Proteins, Macherey-Nagel, Rev. 01, published Mar. 2005, 44 pages.
Frankenne et al: "The Amino Acid Sequence of the Pike (Esox Lucius) Parvalbumin III", FEBS Letters, No. 35, 1973, pp. 145-147.
Reply to Summons to attend oral proceedings filed on Jan. 26, 2017 in opposition proceedings of EP 2 183 049, 11 pages.

* cited by examiner

IMMOBILIZATION OF CHELATING GROUPS FOR IMMOBILIZED METAL ION CHROMATOGRAPHY (IMAC)

This application is a divisional of Ser. No. 12/672,345, filed Feb. 5, 2010, which is a 35 U.S.C. 371 National Phase Entry Application from PCT/EP2008/006485, filed Aug. 6, 2008, which claims the benefit of European Patent Application Nos. 07015389.5 and 08012686.5 filed on Aug. 6, 2007 and Jul. 14, 2008 and which claims the benefit of U.S. Ser. No. 60/954,144 filed Aug. 6, 2007, the disclosures of which are incorporated herein in their entirety by reference.

The present invention refers to a method for binding a polycarboxylic acid to a solid phase. Further, the invention refers to a solid phase having a polycarboxylic acid immobilized thereto and methods of using the solid phase, e.g. for purifying recombinant polypeptides.

A very powerful strategy for purifying recombinant proteins is the use of a "His-tag", which comprises typically 6-10 consecutive histidines. His-tags bind tightly to free coordination sites of $Ni^{2+}$-ions. They can be released by a high concentration of imidazole, which competes for coordination sites on $Ni^{2+}$. Such cycle of specific absorption and desorption can be used for one-step purification of a desired protein, resulting in enrichment factors of 100 or even more.

The most widely used variant of this technique uses $N_\alpha N_\alpha$-bis(carboxymethyl)-lysine coupled via the $\epsilon$-amino group to agarose beads. The active group is NTA (nitrilo triacetic acid) charged with $Ni^{2+}$, while the spacer is an amino butyl group. Such $Ni^{2+}$-NTA-matrix has, however, several serious disadvantages, such as the high costs for $N_\alpha N_\alpha$-bis(carboxymethyl)-lysine.

An additional disadvantage is the instability of the immobilised $Ni^{2+}$-ions. Because NTA has only 4 coordination sites for $Ni^{2+}$, the $Ni^{2+}$ ions leak easily from the matrix and contaminate the protein samples. This is a severe problem for at least two reasons: $Ni^{2+}$ is a rather toxic heavy metal and it catalyses undesired oxidation of the protein sample. Furthermore, NTA-bound $Ni^{2+}$ is easily reduced by protein-protecting agents such as DTT (dithiothreitol) and then released from the matrix. Finally, metal-chelating protease inhibitors such as EGTA or EDTA cannot be combined with a $Ni^{2+}$-NTA-matrix, because they extract the $Ni^{2+}$-ions from this matrix.

U.S. Pat. No. 6,670,159 describes a method for the preparation of metal chelate conjugates based on NTA, wherein NTA or a salt thereof is reacted in an aqueous medium at an alkaline pH of at least 8 with a proteinaceous molecule containing a primary amine group in the presence of carbodiimide.

WO 2004/036189 discloses a separation method for polypeptides using a metal chelate modified support. This support comprises NTA bound to an amino-modified solid phase via a carboxamide group.

GB 2 067 203 discloses polymeric chelating agents comprising a support bound thereto a mixture of EDTA amides bound via a single carboxamide group or via two carboxamide groups. The use of this support for the purification of polypeptides is neither disclosed nor suggested.

US 2004/204569 discloses a His-tag protein comprising a $(His-Asn)_6$-tag.

US 2002/164718 discloses affinity peptides for immobilised metal ion chromatography (IMAC) comprising a spaced His-tag with an amino acid sequence consisting of His, two aliphatic or amide amino acids, His, three basic or acidic amino acids, His, and an aliphatic or amide amino acid.

The object according to the present invention was to provide novel methods and compositions suitable for immobilised metal ion chromatography (IMAC) to circumvent the problems associated with the prior art.

Surprisingly it was found that an EDTA-based solid phase complexed with $Ni^{2+}$, particularly a solid phase wherein a carboxyl group of EDTA is bound to amino groups on the solid phase, has excellent properties in immobilized metal ion chromatography (IMAC) applications, particularly for the purification of recombinant polypeptides comprising poly-histidine tags. This finding was fully unexpected: According to the existing literature, an EDTA-based solid phase should not be suitable for nickel chelate chromatography, because this hexadentate chelator should occupy all six coordinations on $Ni^{2+}$, supposedly leaving none for the binding of a histidine residue. In contrast to this expectation, it was found that an EDTA-based solid phase not only exhibits a stable binding of transition metal ions, particularly of $Ni^{2+}$ ions, but also that the resulting complexes with $Ni^{2+}$, $Zn^{2+}$, $Co^{2+}$ or $Cu^{2+}$ have a high selectivity for histidine-tagged proteins.

A first aspect of the present invention refers to the use of an immobilized chelator having six or more coordination groups for immobilized metal ion chromatography (IMAC), particularly for purification of poly-histidine-tagged proteins. Preferably, the immobilized chelator is a polycarboxylic acid amide or ester having six or more coordination groups, which are particularly selected from amino, carboxyl, carboxamide and hydroxamate groups.

More preferably, the immobilized chelator is a solid phase having a polycarboxylic acid immobilized thereto having a structure of formula (Ia) or (Ib):

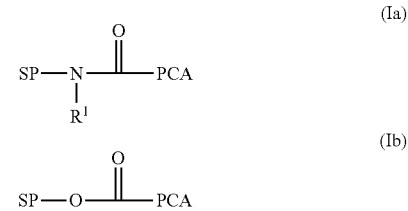

wherein SP is a solid phase;
$R^1$ is hydrogen or an organic residue that does not interfere with the application of the solid phase, e.g. a $C_1$-$C_3$ alkyl radical, and
PCA is the residue of a polycarboxylic acid, particularly of an amino polycarboxylic acid, or a salt thereof.

Even more preferably, the solid phase has a structure of formula (II):

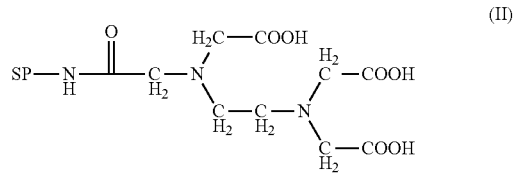

wherein SP is the solid phase; and
one or more of the carboxylic acid groups may be deprotonated.

The solid phase-bound polycarboxylic acid (Ia), (Ib) or (II) may be complexed with a polyvalent metal ion, e.g. a $Ni^{2+}$ ion.

A further aspect of the present invention refers to a method for binding a polycarboxylic acid having 6 or more coordination groups to a solid phase, comprising the steps: (a) providing a polycarboxylic acid and a solid phase comprising amino groups, (b) reacting the amino groups with the polycarboxylic acid in the presence of a condensing agent, wherein the condensing agent is present in a molar excess over the amino groups and the polycarboxylic acid is present in molar excess over the condensing agent and the amino groups, and wherein a single carboxyl group of the polycarboxylic acid reacts with the amino groups.

Still a further aspect of the present invention refers to a solid phase having a polycarboxylic acid immobilized thereto having a structure of formula (Ia) or (Ib):

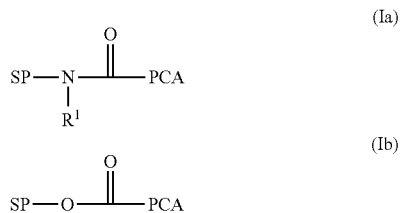

wherein SP is a solid phase;

$R^1$ is hydrogen or an organic residue that does not interfere with the application of the solid phase, e.g. a $C_1$-$C_3$ alkyl radical, PCA is the residue of a polycarboxylic acid, particularly of an amino polycarboxylic acid, or a salt thereof, wherein the immobilized polycarboxylic acid amide or ester has at least 6 or more coordination groups, which are particularly selected from amino, carboxyl, carboxamide and hydroxamate groups, and wherein the surface of the solid phase is preferably substantially free from accessible amino groups, wherein e.g. ≥90%, preferably ≥95% and more preferably ≥99% of the accessible amino groups on the surface of the solid phase are blocked.

In some embodiments of the invention, the carboxamide group —$NR^1$—CO— is directly bound to the solid phase. In other embodiments, the carboxamide group is bound to the solid phase via a linker, which may have a length of 1 atom up to 20 atoms, preferably 2-12 atoms, e.g. 2-6 atoms which may be selected from carbon atoms and optionally heteroatoms such as O and/or N.

Still a further aspect of the present invention is a method of purifying a recombinant polypeptide comprising the steps: (a) providing a sample comprising a polypeptide with a plurality of histidine residues, e.g. a plurality of consecutive histidine residues, (b) contacting the sample with a solid phase as described above that contains a pre-bound complexing metal ion, e.g. a $Ni^{2+}$ ion, under conditions wherein the recombinant polypeptide selectively binds to the solid phase, (c) separating the bound recombinant polypeptide from other sample components, and (d) eluting the recombinant polypeptide from the solid phase.

Still a further aspect of the present invention is a recombinant polypeptide comprising a "spaced histidine tag" with at least 4 histidine residues in a sequence $[H_nS_m]_k$ wherein H is histidine, S is an amino acid residue different from histidine selected from glycine and/or serine and/or threonine, n is in each case independently 1-4, m is in each case independently 1-6, and k is 2-6, preferably 2-5. The spaced histidine tag may have a regular sequence, i.e. n and m have in each occurrence the same value or an irregular sequence, i.e. n and m may have different values. A larger number of histidines within a polyhistidine-tag may increase binding strength and specificity for a $Ni^{2+}$ chelate matrix. Too many consecutive histidines, however, may lower expression levels and solubility of recombinant proteins, e.g. proteins recombinantly expressed in E. coli. These problems can be overcome by interrupting continuous runs of histidines with short spacers comprising glycine, serine and/or threonine, i.e. with a spaced histidine tag. Recombinant proteins, such as nuclear transport receptors or dihydrofolate reductase (DHFR) show higher expression and better solubility during expression in Escherichia coli, when tagged with a spaced histidine tag according to the present invention as compared to a conventional oligo histidine tag.

According to the present invention a method for binding a polycarboxylic acid to a solid phase is provided. The polycarboxylic acid has 6 or more, e.g. 6, 7 or 8 coordination groups. Preferably the polycarboxylic acid has 4, 5 or more carboxylic acid groups. The polycarboxylic acid may be an amino, nitrilo or ether polycarboxylic acid, wherein amino polycarboxylic acids, particularly amino polycarboxylic acids with tertiary amino groups are preferred. Specific examples of polycarboxylic acids are ethylene diamino tetraacetic acid (EDTA), ethylene glycol-bis(2-aminoethylether)-N,N,N',N'-tetraacetic acid (EGTA), diethylene triamino pentaacetic acid (DTPA) and triethylenetetramine-N,N,N',N',N",N" hexaacetic acid (TTHA). Especially preferred is EDTA.

The polycarboxylic acid is preferably bound to a solid phase comprising primary or secondary amino groups. The binding is carried out under conditions which allow selective binding of only one carboxyl group of the polycarboxylic acid to the solid phase without the need of isolating an activated or derivatized form of the polycarboxylic acid such as an anhydride, an active ester, or a form where a primary or secondary amine group of the polycarboxylic acid has been kept accessible for a subsequent coupling step. By means of the reaction between carboxyl group and amino groups a carboxamide bond is formed. The solid phase may, e.g. be an amino-functionalized chromatographic support. For example, the solid phase may be selected from amino-functionalized carbohydrates such as agarose, sepharose, or cellulose, metals or semi-metals such as silicon or oxides thereof such as silica, glass, plastics such as polystyrene or lipids such as phosphatidylethanolamine- or phosphatidylserine-containing phospholipids. Further, the solid phase may comprise particles, e.g. vesicles, magnetic beads, quantum dots, vesicles, or proteins. The amino groups on the solid phase are preferably primary or secondary amino groups, e.g. aliphatic primary amino groups.

The amino-functionalization of the solid phase may be carried out by known methods, e.g. by reacting an amino group-containing silane such as amino propyl triethoxysilane with a solid phase such as silica or glass or by reacting ammonia with an epoxy-activated solid phase. Preferably, the amino-functionalization of silica or glass is carried out with aminopropyl trimethoxy silane or aminopropyl triethoxy silane. Carbohydrates, such as agarose, sepharose, or cellulose are preferably first epoxy-activated e.g. with epichlorohydrine or epibromohydrine to yield epoxy-activated matrices and then treated with excess of ammonia, a primary amine, or a hydroxylamine to yield amino-modified matrices.

The amino group density on the solid phase can be varied by the reaction conditions of the amino-functionalization, e.g. temperature, duration and/or concentration of reactants.

For example, the amino-functionalizing agent may be diluted with a passivating agent, e.g. a non-amino group containing silane, in order to reduce the amino group density on the surface, if necessary. The amino group-containing reactant may be diluted to a concentration of e.g. 1-50% with a passivating agent, preferably with the reaction product between glycidyl oxypropyl trimethoxy silane and 3-mercapto 1,2-propanediol. Alternatively, the amino group density may be increased by using di- or polyfunctional agents, which contain 2 or more primary or secondary amino groups such as 1,13-diamino-4,7,10-trioxatridexane. Thereby, the affinity of the matrix for His-tagged proteins may be increased. Thus, the reaction conditions may be chosen to obtain a final product with desired characteristics, e.g. such that His-tagged proteins bind specifically to the final product, while background-binding of other proteins is minimal. The optimal amino group density may be determined empirically for each solid support according to procedures described in the Examples.

For example, the purification of proteins with a long histidine tag, with e.g. ≥10 histidine residues, is preferably carried out with a surface having a lower density of $Ni^{2+}$-complexed polycarboxylic acid amide groups than purification of proteins having a tag of 6 histidine residues. Conversely, purification under denaturing conditions, e.g. in the presence of guanidinium chloride, is preferably carried out with a higher density of chelating groups than a purification under native conditions.

In the next step, a condensation reaction between one carboxyl group of the polycarboxylic acid and an amino group on the surface is carried out. FIG. 1 shows a schematic depiction of this reaction exemplified with EDTA as polycarboxylic acid.

The reaction is carried out in the presence of a condensing agent, which may be selected from carbodiimides, carbonates such as di(N-succinimidyl)carbonate, O—(N-succinimidyl)-N,N,N',N'-tetramethyluroniumtetrafluoroborate or analogous compounds. Carbodiimides such as 1-ethyl-3-(3-dimethylaminopropyl)carbodiimide (EDC), or N,N'-dicyclohexylcarbodiimide (DCC) are preferred. Reaction conditions were found, where a single carboxyl group of the polycarboxylic acid reacts with the amino groups on the solid phase when the polycarboxylic acid is present in a sufficient molar excess over the amino groups and/or the condensing agent. In preferred embodiment, to obtain a highly specific matrix for IMAC, reaction conditions are selected wherein the amino groups are reacted substantially quantitatively with the polycarboxylic acid. Therefore, an at least 2-fold molar excess, preferably an at least 4-fold molar excess, of the condensing agent and an at least 5-fold excess, preferably an at least 10-fold molar excess and more preferably an at least 25-fold molar excess, of the polycarboxylic acid over amino groups should be used (see Examples).

The reaction is preferably carried out in an aqueous phase. The reaction conditions are preferably pH 5-9, more preferably pH 7-8.5. The polycarboxylic acid is preferably used close to the saturation limit (e.g. 0.5 M for EDTA and 0.1 M for EGTA) and the condensing agent at ⅒-1/50 of the concentration of the polycarboxylic acid.

The reaction product is a solid phase having a polycarboxylic acid immobilized thereto via a stable carboxylic acid amide bond. Preferably, the solid phase has the structure of immobilized formula (Ia) as indicated above. Preferably, the immobilized polycarboxylic acid residue has still at least 3, 4 or more carboxyl groups and optionally further chelating groups such as amino or ether groups.

If the polycarboxylic acid is EDTA the solid phase preferably has a structure of formula (II):

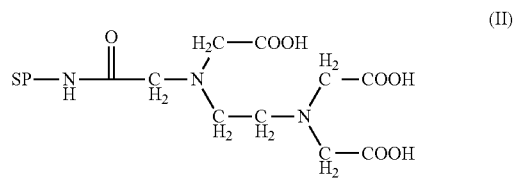

wherein SP is the solid phase.

The solid phase of the invention, e.g. the EDTA-amide solid phase has a high affinity for polyvalent metal ions, such as transition metal ions, e.g. $Ni^{2+}$, $Zn^{2+}$, $Co^{2+}$, or $Cu^{2+}$-ions. Several combinations of these metal ions with chelators immobilized according to this invention provide highly selective matrices for binding histidine-tagged proteins, with less non-specific binding than the traditionally immobilised NTA-group (see FIGS. 2 and 3).

In a preferred embodiment, the solid phase of the invention is substantially quantitatively free from accessible amino groups, e.g. primary amino groups, and/or hydroxy groups, since unreacted amino groups may be cause of low affinity $Ni^{2+}$ binding and high unspecific background binding of polypeptides not carrying a His-tag. Thus, it may be desirable that ≥90%, preferably ≥95% and more preferably ≥99% of accessible amino groups, particularly primary amino groups on the surface of the solid phase are blocked, e.g. by reaction with the polycarboxylic acid mediated by the condensing agent. The quantity of accessible unreacted groups, e.g. primary amino groups, may be determined according to known methods, e.g. by a ninhydrin-test or an OPA (ortho-phthalaldehyde/mercaptane) reaction.

Further, it is preferred that the solid phase, e.g. the EDTA-amide solid phase, is substantially free from loosely bound polyvalent metal ions, such as $Ni^{2+}$ ions. The present inventors have found that when initially saturating an EDTA-amide matrix with $Ni^{2+}$ ions, a significant amount thereof may remain only loosely bound thereto, in particular, when the solid support still contains unreacted amine groups. This loosely bound $Ni^{2+}$ fraction may be detected with suitable reagents, e.g. dimethylglyoxime. For example, after adding 0.2-1 volumes of 1% w/v dimethylglyoxime dissolved in ethanol to an $Ni^{2+}$ loaded matrix in Tris-buffer pH7.5 and shaking the mixture for 15 minutes at 60° C., any loosely bound $Ni^{2+}$ ions can be detected as a pink precipitate. Loosely bound metal ions may cause problems, namely a contamination of a protein-containing sample with toxic and oxidizing $Ni^{2+}$ ions and an increased non-specific binding of non-His-tag proteins.

Figure 4:
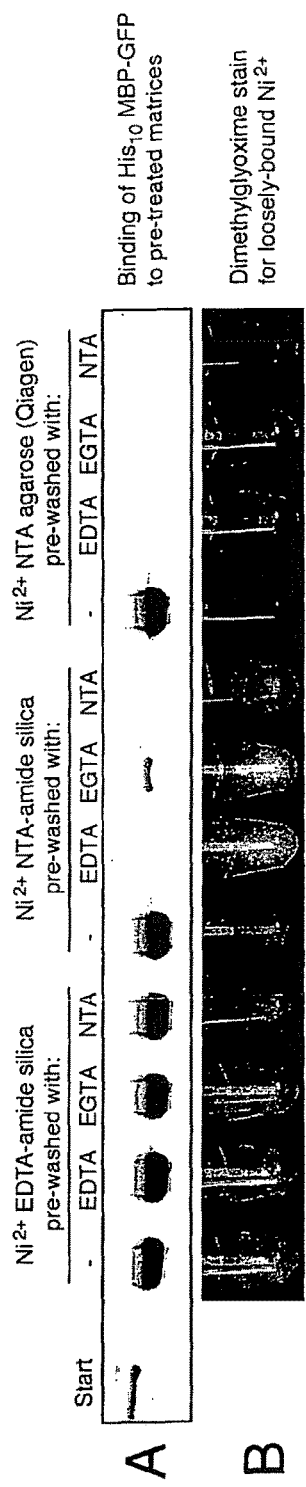

Thus, the solid phase of the present invention is preferably substantially free from loosely bound metal ions, particularly loosely bound $Ni^{2+}$ ions. Loosely bound metal ions may, e.g. be removed from the solid phase by contacting the solid phase with a free polycarboxylic acid chelator, e.g. NTA or EGTA or EDTA, preferably at about pH 7.5, e.g. with 40 mM NTA or 10 mM EGTA or 10 mM EDTA, until loosely bound metal ions have become undetectable, e.g. by contacting the matrix with a suitable detection reagent for the respective metal ion, e.g. dimethylglyoxime for the detection of $Ni^{2+}$ ions. After removal of loosely bound metal ions, the remaining ions remain so tightly bound that even an overnight incubation at room temperature with an equal volume of 0.5 M EDTA (pH 7.5) is insufficient for a complete release from the EDTA-amide matrix. In contrast, it should be noted that pre-washing of commercially available Ni-NTA-agarose (Qiagen) or of an Ni-NTA-amide matrix with 40 mM NTA, or 10 mM EGTA or 10 mM EDTA removes not only loosely bound, but apparently all bound $Ni^{2+}$ ions (FIG. 4).

Surprisingly, no indication was found that the conversion of one carboxyl group in EDTA to a carboxamide group would weaken the affinity for $Ni^{2+}$ at neutral pH. Instead, the carbonyl oxygen or the amino group of the carboxamide can apparently engage in a coordinative bond to $Ni^{2+}$, suggesting that EDTA-amide is a truly hexadentate chelator. That a carboxamide groups can coordinate $Ni^{2+}$ is evident, e.g., from methyl coenzyme M-reductases, where 4 coordination sites for $Ni^{2+}$ are provided by Coenzyme F430 and the $5^{th}$ by the carboxamide of a glutamine side chain (Ermler et al, Science 278 (1997), 1457).

The solid phase of the invention may be used for immobilized metal ion chromatography (IMAC). In this chromatographic method polypeptides comprising a plurality of histidine residues, e.g. consecutive histidine residues, e.g. at least six consecutive histidine residues are selectively bound to a metal complex solid phase of the present invention and separated from other components. The polypeptide may be eluted from the solid phase by adding a suitable elution agent such as imidazole. The imidazole concentration is preferably in the range from 1 to 1000 mM, depending on the density of immobilised active groups, the length of the poly-histidine tag, and the multimeric state of the tagged protein.

For IMAC purification of His-tagged proteins to work, it was so far assumed that the immobilised chelator should occupy only 3-5 out of the 6 coordination sites of $Ni^{2+}$. It is therefore an unexpected aspect of this invention that immobilised hexadentate chelators such as EDTA-amide or EDTA-hydroxamide and even chelators with more than 6 coordinating groups work extremely well for this application. Apparently, histidine side chains can transiently displace weakly coordinating groups within a given chelator. Thus, according to an embodiment of the invention, the immobilized chelator, i.e. the immobilized polycarboxylic acid amide has 6 or more coordination groups, particularly selected from amino, carboxyl, carboxamide, and hydroxamate groups.

On the solid phase of the invention, e.g. EDTA-amide, kinetically very stable complexes e.g. with $Ni^{2+}$ may be formed. The resulting matrices are extremely resistant to $Ni^{2+}$-extraction, e.g. by EGTA or NTA. Even 0.5 M EDTA extracts $Ni^{2+}$ only very slowly, i.e. at a time scale of hours to days. The resistance towards $Ni^{2+}$-extraction increases further by including imidazole, e.g. 1 mM imidazole in the buffer. Therefore, IMAC with a solid phase of the invention, e.g. an EDTA-amide matrix, can be performed in the presence of a chelating metalloprotease-inhibitor, e.g. EDTA in concentrations of 1-10 mM, e.g. 5 mM.

Traditional Ni-chelate matrices, such as Ni-NTA agarose, get easily reduced by protein-protecting agents such as dithiothreitol (DTT). Even low millimolar concentrations of DTT extract nickel in the form of brownish reduction products. In contrast, $Ni^{2+}$ EDTA-amide matrices, from which loosely-bound $Ni^{2+}$ had been removed, do not show these problems. Instead, on $Ni^{2+}$ EDTA-amide silica we could successfully purify his-tagged proteins in the presence of extremely high concentrations of DTT, e.g. of 0.5 M or 1 M DTT (FIG. 5), which is a 100-1000-fold higher DTT concentration than used in typical protein purification schemes. Thus, in a preferred embodiment, the metal ion, e.g. $Ni^{2+}$ ion containing solid phase of the invention is stable in the presence of a thiol-containing or dithiol-containing reducing agent, e.g., DTT, in a concentration of at least 10 mM, preferably of at least 20 mM, more preferably of at least 50 mM, and even more preferably of at least 100 mM or even of at least 500 mM, and up to 1000 mM or even higher, preferably for at least 1 h at room temperature.

In an especially preferred embodiment of the present invention the chromatography is carried out with a recombinant polypeptide comprising a plurality of histidine residues in a "spaced histidine tag", preferably in a sequence $[H_nS_m]_k$ wherein H is histidine, S a spacer residue selected from glycine and/or serine and/or threonine, n is 1-4, m is 1-6, preferably 1-4, and k is 2-8, preferably 2-6. The length of the tag is preferably from 8 to 50 amino acids, more preferably from 12 to 40 amino acids. The present invention also comprises irregularily-spaced histidine tags, where the lengths of the oligo histidine clusters and the lengths of the spacer regions vary within a given tag sequence. The spaced histidine tag is preferably located at the N- and/or at the C-terminus of the recombinant polypeptide and/or inserted into the sequence of the recombinant polypeptide.

Further, the invention is explained in more detail by the following Figures and Examples.

FIGURE LEGENDS

FIG. 1: Scheme for the coupling of EDTA to an amine-containing support. The reaction is carried out under conditions where a selective reaction occurs between a single carboxyl group of EDTA with the amino group on the support.

Figure 2:
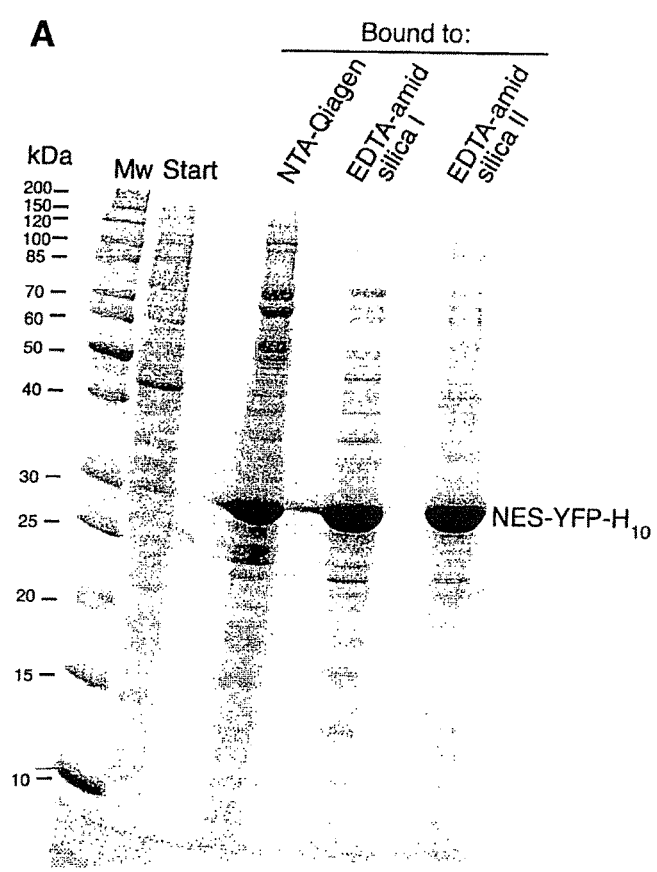
Figure 2:
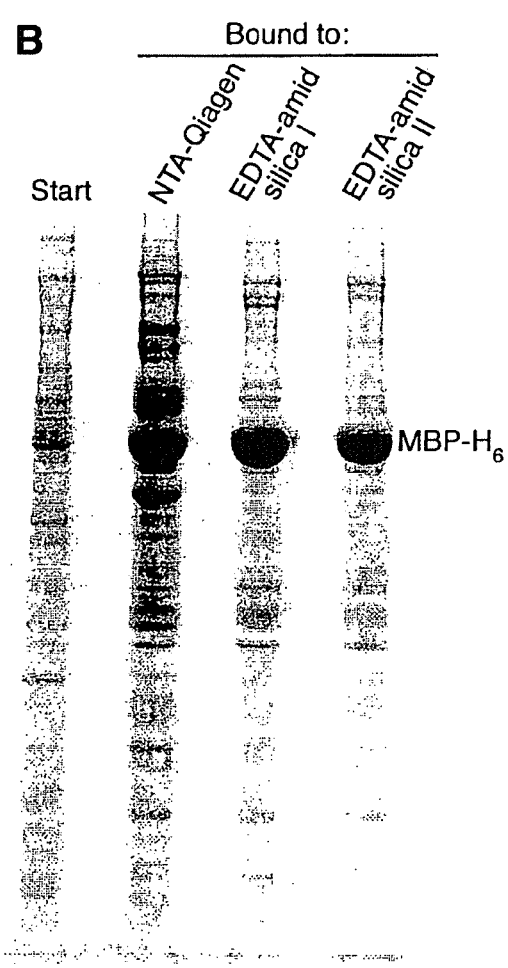
Figure 2:
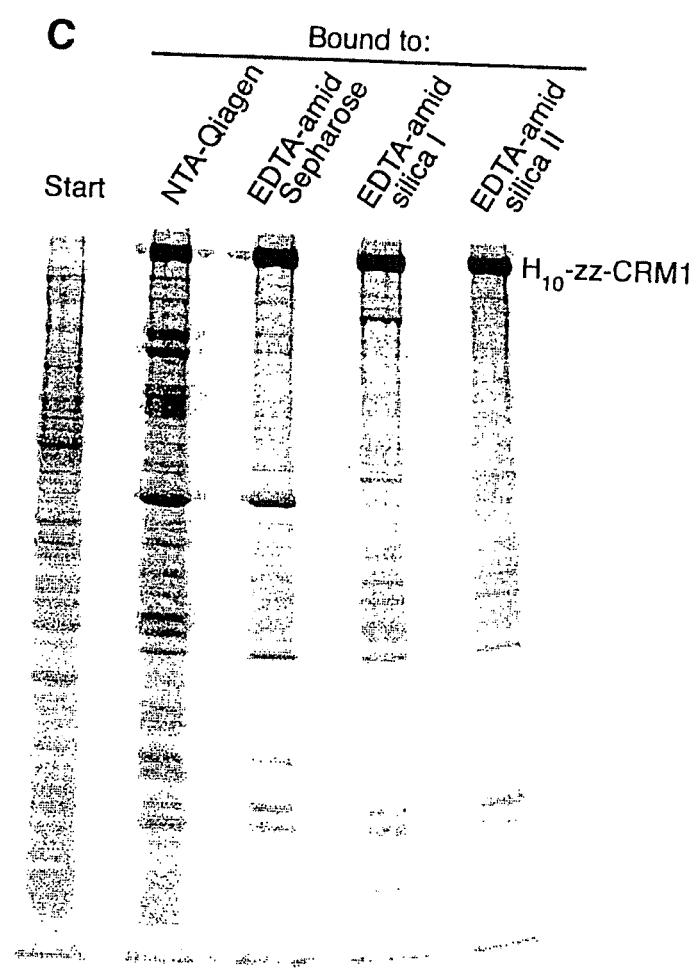

FIG. 2: Comparison of the protein binding specificity of various $Ni^{2+}$-containing chromatographic matrices in IMAC.

The protein binding characteristics of various His-tagged proteins, namely a comparative matrix (NTA-Qiagen) and three inventive matrices (EDTA-amide silica I, EDTA-amide silica II and EDTA-amide sepharose) are shown (cf. Example 5 for details).

Figure 3:
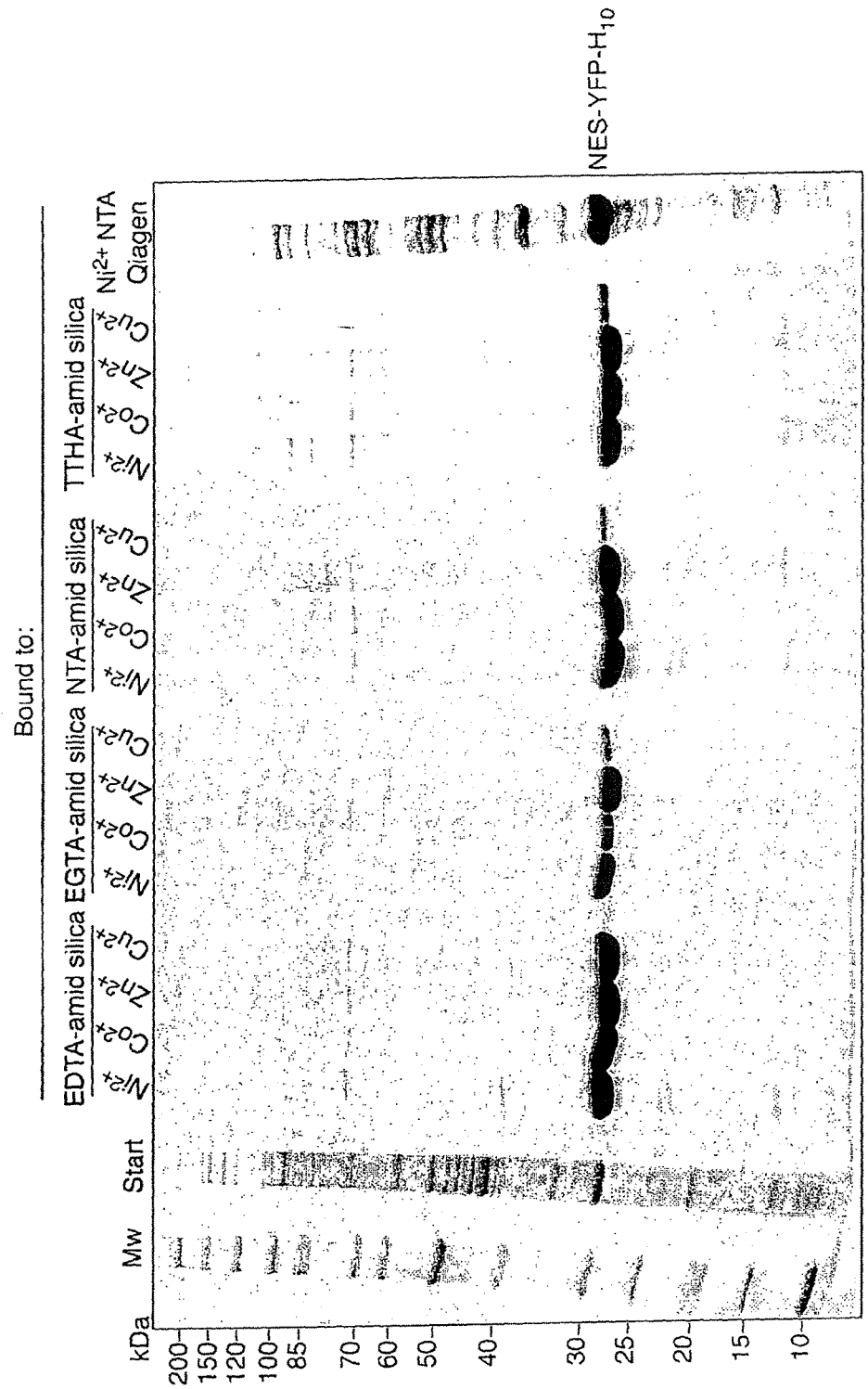

FIG. 3: Combination of various chelators and transition metal ions for IMAC.

The protein binding properties of various matrices (inventive EDTA, EGTA and TTHA matrices and an NTA matrix) with different chelators in the presence of various transition metal ions are shown (cf. Example 6 for details).

FIG. 4: Resistance of Ni-chelate matrices against extraction of $Ni^{2+}$ by free chelators.

The strength of $Ni^{2+}$ binding to an inventive EDTA-amide matrix and comparative NTA matrices is shown (cf. Example 7 for details).

Figure 5:
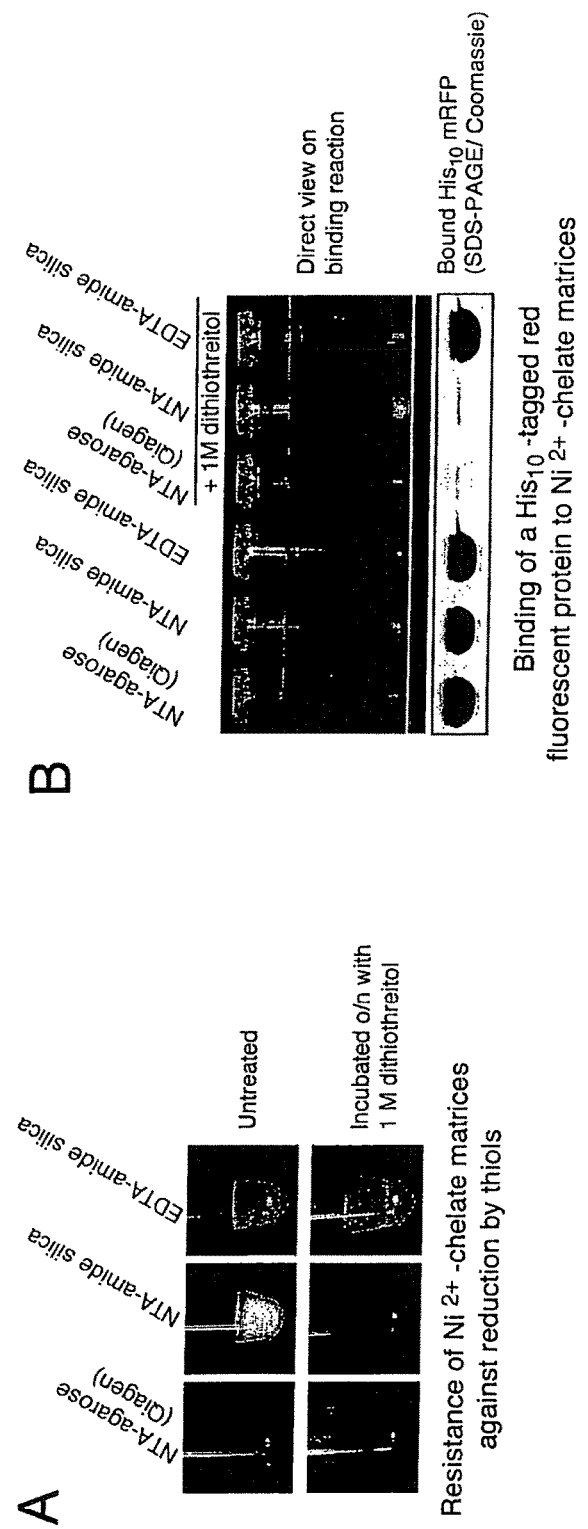

FIG. 5: Resistance of various Ni-chelate matrices against thiol-containing reducing agents.

The resistance of various $Ni^{2+}$ containing chelator matrices (an inventive EDTA-amide matrix and comparative NTA matrices) against $Ni^{2+}$ extraction and reduction in the presence of DTT is shown (cf. Example 8 for details).

Figure 6:
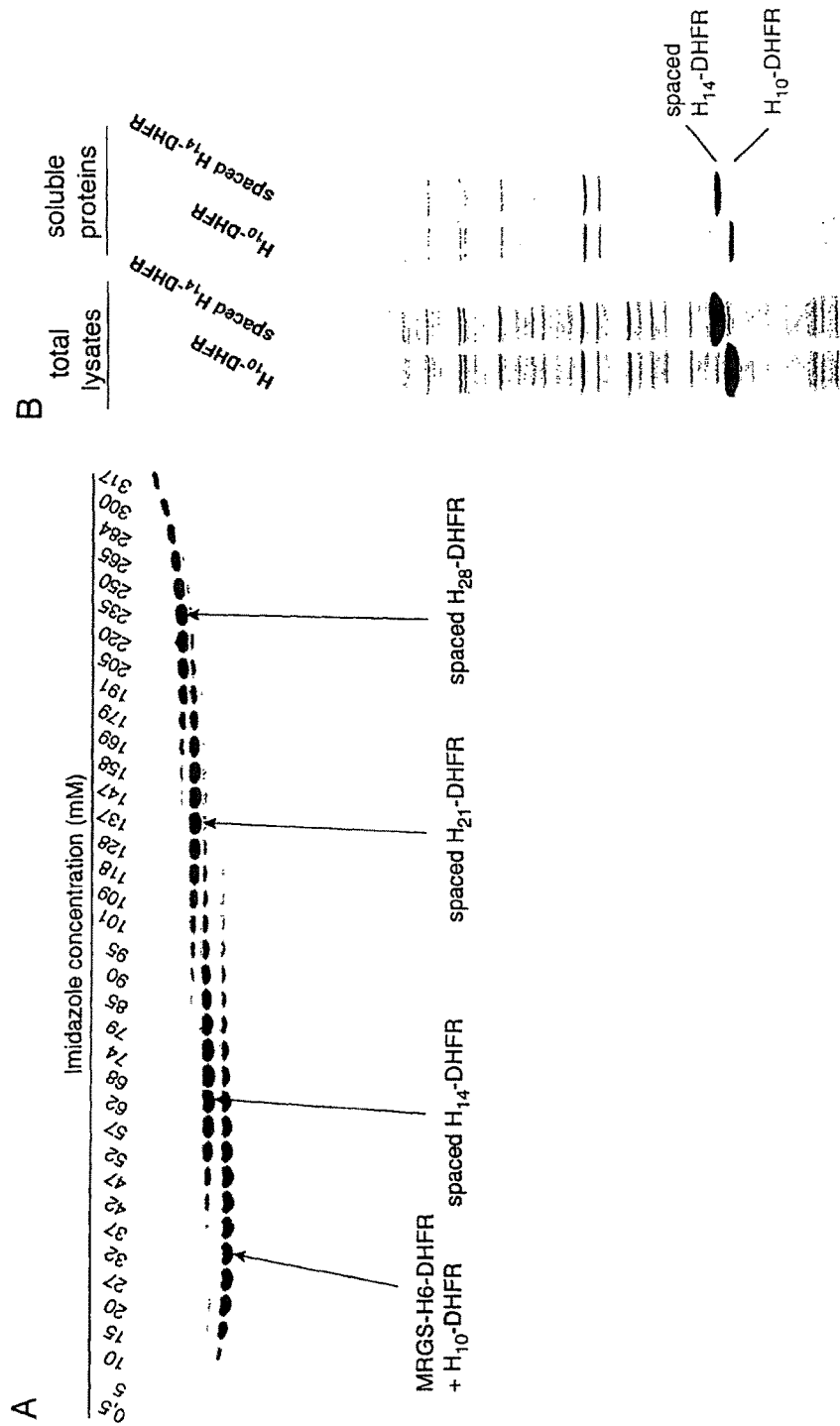

FIG. 6: Characterisation of spaced poly-histidine tags.

A) The binding characteristics of inventive spaced poly-His tags (spaced H14, spaced H21 and spaced H28) and comparative His tags (MRGS6 and H10) are shown.

B) The expression of proteins containing an inventive spaced His-tag and a comparative His-tag (H10) are shown (cf. Example 9 for details).

EXAMPLES

Example 1

Preparation of Ni-EDTA-Amide Sepharose 4B 1 liter Sepharose 4B is prewashed on a glass-funnel with 1 liter 0.1 M NaOH (in water), followed by 5 times one liter of pure water, transferred to a 5 liter flask, and filled up with water to a volume of 2 liters. 0.8 mol of NaOH are added, the temperature adjusted to 25° C., followed by addition of 1.0 mol epibromhydrine. The mixture is then shaken for 2 hours at 25° C., and then chilled on ice. The resulting epoxy-activated Sepharose is subsequently recovered by filtration through a glass funnel, washed with water, and resuspended in 2 M $NH_4Cl$ (final concentration in water, final volume 2 liters). 4 mol $NH_3$ are added from a 25% aqueous solution and the mixture is shaken o/n at room temperature.

The resulting $NH_2$-Sepharose 4B is recovered by filtration, washed with water until free $NH_3$ has be become undetectable, and resuspended in 0.5 M EDTA/$Na^+$ pH 8.0 (final concentration, final volume 2 liters). Then, 50 mmol EDC are added and the mixture is shaken for 1 hour at room temperature. Thereafter, another 50 mmol EDC aliquot is added and the reaction is allowed to proceed o/n.

The resulting EDTA-amide Sepharose is recovered by filtration and washed until the free EDTA-concentration has dropped below 1 mM. The Sepharose is then charged with 20 mM $NiCl_2$ in Tris buffer pH 7.5, until free $Ni^{2+}$ appears in the non-bound fraction. Free and loosely-bound $Ni^{2+}$ ions are then removed by washing with water, 10 mM NTA pH 7.5, water, and is finally resuspended in 30% ethanol+10 mM imidazole/HCl+1 mM NTA pH 7.5 for long-term storage.

The properties of the $Ni^{2+}$ EDTA-amide Sepharose can be adjusted by varying the epoxy-activation step. Coupling at higher temperature (up to 40° C.) and using higher concentrations of epichlorhydrine and NaOH (up to 1.2 M epichlorhydrine and 1.0 M NaOH, respectively) will result in higher coupling-density, but also in higher background-binding. Lower temperature (down to 18° C.) using a lower concentration of epichlorhydrine and NaOH (down to 0.2 M epichlorhydrine and 0.1 M NaOH, respectively) will result in lower coupling density, and in even lower background binding, but also in lower specific binding capacity, in particular for proteins with short His-tags.

Example 2

Preparation of EDTA-Amide Magnetic Beads 5 ml of amine-terminated magnetic beads (Sigma #17643-5 ml) are washed in water and resuspended in a final volume of 5 ml in 0.5 M EDTA/$Na^+$ pH 8.0. A 125 µmol EDC aliquot is added and the reaction is shaken for 1 hour at room temperature. Thereafter, another 125 µmol EDC aliquot is added and the reaction is continued o/n.

The resulting EDTA-amide magnetic beads are recovered by magnetic separation, washed with water, and charged with $Ni^{2+}$ or another metal ion analogously to Example 1.

Example 3

Preparation of High-Density EDTA-Amide Silica 100 g Davisil XWP1000 Å 90-130 (Grace) are resuspended in 500 ml of 3% (v/v) aminopropyl triethoxy silane, 4% water, 93% ethanol and shaken gently for 2 hours at 40° C. and then o/n at room temperature. The amino-modified silica is recovered by filtration and free silane is removed by washing with pure water. Covalent coupling to EDTA and charging with $Ni^{2+}$ are performed as described for Sepharose 4B. For long term-storage, the product can be dried out of water or isopropanol.

Example 4

Preparation of EDTA-Amide Silica with a Passivated Surface

The $Ni^{2+}$ EDTA-amide silica from Example 3 three still suffers from high background-binding when used in IMAC. This background may probably result from residual silanol- and amino groups (which for sterical reasons could not react with the activated EDTA) and/or from high surface concentrations of EDTA-amide. The background-problem can be solved by including a passivating silane during the modification of silica with aminopropyl-silane. The so far best passivating silane is the reaction product between glycidyl oxypropyl trimethoxy silane and 3-mercapto 1,2-propandiol.

3 ml glycidyl oxypropyl trimethoxy silane are mixed with 3 ml 2-mercapto 1,3-propandiol, 90 ml methanol, 4 ml water and 10 µl 4-methyl morpholine, and the reaction is allowed to proceed for 30 minutes at 25° C. 150 µl aminopropyl trimethoxy silane are added, and the resulting mixture is used to modify 30 g Davisil XWP1000 Å 90-130 as described above. The ratio between the aminosilane and the passivating silane is in this example defined as 5%. It can, however, be varied between 1% and 50%. The resulting passivated amino-silica is then reacted with EDTA or another chelating group, charged with metal ions, and treated to remove loosely-bound metal ions as described above.

Example 5

Comparison of $Ni^{2+}$-Containing Chromatographic Supports in IMAC

The following chromatographic supports were tested:

| | |
|---|---|
| "NTA-Qiagen": | $Ni^{2+}$-NTA Agarose purchased from Qiagen |
| "EDTA-amide silica I": | $Ni^{2+}$-charged EDTA-amide silica with 20% coupling density (Example 4) |
| "EDTA-amide silica II": | $Ni^{2+}$-charged EDTA-amide silica with 5% coupling density (Example 4) |
| "EDTA-amide Sepharose ": | $Ni^{2+}$-charged EDTA-amide Sepharose 4B (Example 1) |

E. coli cells were resuspended in buffer (50 mM Tris/HCl pH 7.5, 2 mM magnesium acetate, 50 mM NaCl, 5 mM mercaptoethanol). A lysate was prepared and cleared by ultracentrifugation. Then, either 1 µM of a fusion protein ("NES-YFP-$H_{10}$") comprising a nuclear export signal (NES), the yellow fluorescent protein (YFP) and a C-terminal deca His-tag, or 1 µM of a fusion between the maltose binding protein (MBP) with a C-terminal hexa His-tag ("MBP-$H_6$"), or 0.5 µM of a fusion protein containing a deca His-tag, a zz-tag and the mouse exportin CRM1 ("$H_{10}$-zz-CRM1") were added and used as starting materials for the binding experiments. For purification of the deca-His-tagged proteins, starting materials were supplemented with 1 mM imidazole.

400 µl starting material each were rotated o/n at 4° C. with 10 µl chromatographic support. After washing with 5 ml buffer, bound proteins were eluted with 0.4 M imidazole pH 7.5. Analysis was by SDS-PAGE on 12% acrylamide gel, followed by Coomassie-staining. The load corresponds to 0.5 µl matrix.

FIG. 2 shows the results for NES-YFP-$H_{10}$ (panel A), MBP-$H_6$ (panel B) and $H_{10}$-ZZ-CRM1 (panel C). All tested matrices exhibit efficient binding of His-tagged proteins. The matrices of the present invention however show significantly lower backgrounds compared to the NTA-Qiagen matrix.

Example 6

Testing of Various Chelators and Transition Metal Ions for IMAC

Amino-silica with 5% coupling density (as described in Example 4) was conjugated with either EDTA, EGTA, NTA, or TTHA. Each of the resulting matrices was then charged with either $Ni^{2+}$, $Co^{2+}$, $Zn^{2+}$, or $Cu^{2+}$. The binding assays for NES-YFP-$H_{10}$ were performed as described in Example 5, however, 100 mM NaCl were included in the wash buffer.

FIG. 3 shows that the tested combinations of matrices and metal ions show efficient binding of NES-YFP-$H_{10}$.

Example 7

Resistance of Ni-Chelate Matrices Against Extraction of $Ni^{2+}$ by Free Chelators Each 1 ml of $Ni^{2+}$-EDTA-amide silica (50% coupling density; prepared according to Example 4), $Ni^{2+}$-NTA-amide silica (50% coupling density), or $Ni^{2+}$-NTA-agarose (Qiagen) were washed over a time of 45 min with either 30 ml Tris-buffer, or 10 mM EDTA pH 7.6, or 10 mM EGTA pH 7.6, or 40 mM NTA pH 7.6, followed by equilibration in binding buffer (50 mM Tris/HCl pH 7.5, 500 mM NaCl, 5 mM $MgCl_2$). 10 µl of each pre-treated matrix was then used to bind a $His_{10}$-MBP-GFP fusion (10 µM concentration) out of 600 µl E. coli lysate. The bound fraction was eluted with 75 µl 1 M imidazol/HCl pH 7.5. 1 µl of each eluate was then analysed by SDS-PAGE followed by Coomassie-staining. The results are shown in FIG. 4A. The inventive $Ni^{2+}$-EDTA-amide silica matrix was completely resistant against all tested chelator-solutions. The comparative matrices were significantly less resistant. $Ni^{2+}$-NTA-agarose was discharged by any of the chelator-treatments. $Ni^{2+}$-NTA-amide silica was completely discharged by 10 mM EDTA and 40 mM NTA, but retained a small activity after treatment with EGTA.

The chelator-washed matrices from the panel shown in FIG. 4A were equilibrated in 100 mM Tris/HCl pH 7.5, mixed with an equal volume of 1% dimethylglyoxime (dissolved in Ethanol) and incubated for 15 min at 60° and subsequently o/n at room temperature, before photographs were taken. The results are shown in FIG. 4B. A pink dimethylglyoxime-$Ni^{2+}$ precipitate, representing loosely-bound $Ni^{2+}$, occurred with untreated $Ni^{2+}$-NTA-amide silica and with untreated $Ni^{2+}$-NTA agarose, but not with the inventive $Ni^{2+}$-EDTA-amide silica. Pre-washing of $Ni^{2+}$-NTA-amide silica or of $Ni^{2+}$-NTA agarose with the above-mentioned chelators removed loosely-bound $Ni^{2+}$ to the same extent as it reduced the capacity to bind the histidine-tagged protein.

Thus, the binding of $Ni^{2+}$ ions to the inventive EDTA-amide matrix is significantly stronger than to comparative NTA matrices.

Example 8

Resistance of Ni-Chelator Matrices Against Thiol-Containing Reducing Agents

The resistance of various $Ni^{2+}$ containing chelator matrices against dithiothreitol (DTT), a thiol-containing reducing agent, was tested.

NTA-agarose (Qiagen), NTA-amide silica and EDTA-amide silica were either left untreated or were incubated o/n at room temperature with 1 M DTT, buffered with 1 M Tris/HCl pH 7.5. The results are shown in FIG. 5A. The DTT treatment converted $Ni^{2+}$ from NTA-agarose (Qiagen) and NTA-amide silica into brownish reduction products. In contrast, $Ni^{2+}$ EDTA-amide silica remained fully unaffected.

The above matrices (≈50 µl) were resuspended in either 1 ml 1 M Tris/HCl pH 7.5 or 1 M Tris/HCl pH 7.5+1 M DTT. 5 min later, a $His_{10}$-tagged red fluorescent protein was added and the binding reactions were rotated o/n at room temperature. The matrices were allowed to sediment by gravity and photographs were taken. The results are shown in FIG. 5B (upper panel). Red colour on the beads indicates binding of the his-tagged protein. In the absence of DTT, all matrices bound the his-tagged protein very well. The DTT-treatment fully abolished binding to $Ni^{2+}$ NTA agarose (Qiagen) and $Ni^{2+}$ NTA-amide silica. The non-bound fractions contained brownish reduction products of $Ni^{2+}$ that were released from the beads. In contrast, binding of the His-tagged red fluorescent protein to the inventive $Ni^{2+}$ EDTA amide silica remained unaffected by the DTT treatment.

The bound fractions were eluted with 1 M imidazol pH 7.3, and analysed by SDS-PAGE followed by Coomassie staining. The results are shown in FIG. 5B (lower panel). The analysis confirmed that 1 M DTT completely abolished binding of the his-tagged protein to $Ni^{2+}$ NTA-agarose or $Ni^{2+}$ NTA-amide silica, while binding to the inventive $Ni^{2+}$ EDTA-amide silica was not affected at all.

Example 9

Characterisation of Spaced Poly-Histidine Tags

A mixture of DHFR derivatives tagged with various histidine tags was bound to $Ni^{2+}$ EDTA amide silica and eluted slowly with a gradient of increasing imidazole concentration. The results are shown in FIG. 6A. (Actual concentrations are given above the lanes). Panel shows analysis of eluted fractions by SDS-PAGE/Coomassie-staining. Tags with greater number of histidines confer tighter binding to the matrix, elution at higher imidazole concentration, and thus better separation from contaminants that are not poly-histidine tagged. The following tags have been used (amino acids in single letter code):

```
                                               (SEQ ID NO: 1)
MRGS6 = MRGSHHHHHH (SEQ ID NO: 2)
H10 = MHHHHHHHHHH (SEQ ID NO: 3)
spaced H14 = MSKHHHHSGHHHTGHHHHSGSHHH
```

-continued (SEQ ID NO: 4)
spaced H21 = MSKHHHHSGHHHTGHHHHSGSHHHTGHHHHSGSHHH (SEQ ID NO: 5)
spaced H28 = MSKHHHHSGHHHTGHHHHSGSHHHTGHHHHSGSHHH
TGHHHHSGSHHH Although His-tags with more histidines confer a more specific binding to Ni-chelate matrices, they pose the problem that continuous stretches of too many histidines compromises expression levels and solubility in *E. coli*. Interrupting continuous polyhistidine stretches with Gly, Ser, and/or Thre-containing spacers rectifies these problems. In the representative example shown, tagging of DHFR with a spaced $His_{14}$ tag doubled the yield of soluble protein during recombinant expression in *E. coli* as compared to a conventional, continuous $His_{10}$ tag (FIG. 6B).

The invention claimed is:

1. A solid phase having a polycarboxylic acid immobilized thereto having a structure of formula (I):

wherein SP is a solid phase; and
PCA is the residue of a polycarboxylic acid, or a salt thereof, wherein the immobilized polycarboxylic acid ester has at least 6 or more coordination groups
and wherein ≥90% of the accessible hydroxy groups on the surface of the solid phase are blocked.

2. The solid phase of claim 1, wherein PCA is the residue of EDTA or a salt thereof.

3. The solid phase of claim 1, wherein the polycarboxylic acid residue is complexed with a metal ion.

4. The solid phase of claim 3, which is stable in the presence of a thiol- or dithiol-containing reducing agent.

5. The solid phase of claim 1, wherein the PCA is the residue of an amino polycarboxylic acid, or a salt thereof.

6. The solid phase of claim 1, wherein the coordination groups are selected from the group consisting of amino, carboxyl, carboxamide, and hydroxamate groups.

7. The solid phase of claim 1, wherein ≥95% of the accessible hydroxy groups on the surface of the solid phase are blocked.

8. The solid phase of claim 1, wherein ≥99% of the accessible hydroxy groups on the surface of the solid phase are blocked.

9. The sold phase of claim 3, wherein the metal ion is a transition metal ion.

10. The solid phase of claim 3, wherein the metal ion is a $Ni^{2+}$ ion.

* * * * *

SEQUENCE LISTING

<160> NUMBER OF SEQ ID NOS: 5

<210> SEQ ID NO 1
<211> LENGTH: 10
<212> TYPE: PRT
<213> ORGANISM: Artificial
<220> FEATURE:
<223> OTHER INFORMATION: His-tag MRGS6

<400> SEQUENCE: 1

Met Arg Gly Ser His His His His His His
1               5                   10

<210> SEQ ID NO 2
<211> LENGTH: 11
<212> TYPE: PRT
<213> ORGANISM: Artificial
<220> FEATURE:
<223> OTHER INFORMATION: His-tag H10

<400> SEQUENCE: 2

Met His His His His His His His His His His
1               5                   10

<210> SEQ ID NO 3
<211> LENGTH: 24
<212> TYPE: PRT
<213> ORGANISM: Artificial
<220> FEATURE:
<223> OTHER INFORMATION: His-tag "spaced H14"

<400> SEQUENCE: 3

Met Ser Lys His His His His Ser Gly His His His Thr Gly His His
1               5                   10                  15

His His Ser Gly Ser His His His
            20

<210> SEQ ID NO 4
<211> LENGTH: 36
<212> TYPE: PRT
<213> ORGANISM: Artificial
<220> FEATURE:
<223> OTHER INFORMATION: His-tag "spaced H21"

<400> SEQUENCE: 4

Met Ser Lys His His His His Ser Gly His His His Thr Gly His His
1               5                   10                  15

His His Ser Gly Ser His His His Thr Gly His His His His Ser Gly
            20                  25                  30

Ser His His His
        35

<210> SEQ ID NO 5
<211> LENGTH: 48
<212> TYPE: PRT

```
-continued

<213> ORGANISM: Artificial
<220> FEATURE:
<223> OTHER INFORMATION: His-tag "spaced H28"

<400> SEQUENCE: 5

Met Ser Lys His His His His Ser Gly His His Thr Gly His His
1               5                  10                  15

His His Ser Gly Ser His His Thr Gly His His His His Ser Gly
            20                  25                  30

Ser His His Thr Gly His His His Ser Gly Ser His His His
        35                  40                  45
```